United States Patent
Nakagawa et al.

(10) Patent No.: US 9,820,649 B2
(45) Date of Patent: Nov. 21, 2017

(54) VOLUME MEASURING DEVICE, VOLUME MEASURING METHOD, AND VOLUME MEASURING PROGRAM FOR THREE-DIMENSIONAL TOMOGRAPHIC IMAGE

(71) Applicant: KOWA COMPANY, LTD., Nagoya-shi, Aichi (JP)

(72) Inventors: Toshiaki Nakagawa, Higashimurayama (JP); Yoshihiro Kakutani, Higashimurayama (JP); Masaharu Mizuochi, Higashimurayama (JP)

(73) Assignee: KOWA COMPANY, LTD. (JP)

( * ) Notice: Subject to any disclaimer, the term of this patent is extended or adjusted under 35 U.S.C. 154(b) by 0 days.

(21) Appl. No.: 15/300,191

(22) PCT Filed: Mar. 30, 2015

(86) PCT No.: PCT/JP2015/059848
§ 371 (c)(1),
(2) Date: Sep. 28, 2016

(87) PCT Pub. No.: WO2015/152119
PCT Pub. Date: Oct. 8, 2015

(65) Prior Publication Data
US 2017/0135578 A1    May 18, 2017

(30) Foreign Application Priority Data

Mar. 31, 2014   (JP) .................................. 2014-072642

(51) Int. Cl.
*A61B 3/14* (2006.01)
*A61B 3/12* (2006.01)
(Continued)

(52) U.S. Cl.
CPC .......... *A61B 3/1225* (2013.01); *A61B 3/0025* (2013.01); *A61B 3/0041* (2013.01); *A61B 3/102* (2013.01)

(58) Field of Classification Search
CPC ..... A61B 3/1005; A61B 3/102; A61B 3/1025; A61B 3/12; A61B 3/1225; A61B 5/0066
(Continued)

(56) References Cited

U.S. PATENT DOCUMENTS

2006/0087615 A1    4/2006 Kojima et al. ................ 351/206
2012/0002164 A1    1/2012 Yamamoto et al. .......... 351/206

FOREIGN PATENT DOCUMENTS

JP    2006122160    5/2006
JP    2006334044    12/2006
(Continued)

OTHER PUBLICATIONS

International Search Report dated Jun. 16, 2015 issued in International Application No. PCT2015/059848 together with English-language translation thereof.

*Primary Examiner* — Mahidere Sahle
(74) *Attorney, Agent, or Firm* — Adams & Wilks

(57) ABSTRACT

A three-dimensional tomographic image (B) is formed which is composed of a plurality of two-dimensional tomographic images obtained by scanning an ocular fundus. A contour of a certain 2D region (M1, M2, M3, M4) in the tomographic image is determined for each tomographic image, and the volume of a certain 3D region is calculated through correcting each area of the certain 2D region defined by the determined contour or its accumulated value using an image correction coefficient in accordance with the diopter of the subject's eye. Even for subjects' eyes of different
(Continued)

diopters, the influence of the diopter correction is eliminated and a quantitative comparison of subjects' eyes of different diopters is possible.

6 Claims, 6 Drawing Sheets

(51) Int. Cl.
    *A61B 3/00*     (2006.01)
    *A61B 3/10*     (2006.01)

(58) Field of Classification Search
    USPC .......................................................... 351/206
    See application file for complete search history.

(56) References Cited

FOREIGN PATENT DOCUMENTS

| | | |
|---|---|---|
| JP | 2009000354 | 1/2009 |
| JP | 2012011142 | 1/2012 |

# VOLUME MEASURING DEVICE, VOLUME MEASURING METHOD, AND VOLUME MEASURING PROGRAM FOR THREE-DIMENSIONAL TOMOGRAPHIC IMAGE

TECHNICAL FIELD

The present invention relates to a volume measuring device, a volume measuring method, and a volume measuring program for a three-dimensional tomographic image which measure the volume of a certain region of the three-dimensional tomographic image composed of a plurality of tomographic images of an ocular fundus obtained by optical coherence tomography.

BACKGROUND ART

Tomographic image capturing devices are put into practical use. Such a device captures tomographic images of an ocular fundus using the principle of optical coherence tomography (OCT).

In a process of treatment for a patient who suffers from lesion of ocular fundus, the volume of the site of lesion may have to be regularly measured to estimate the medicinal effect. Measuring the volume of the site of lesion using tomographic images includes configuring a three-dimensional tomographic image from a plurality of B-scan images (tomographic images) obtained by scanning the ocular fundus, manually setting contours of the site of lesion in the B-scan images, and calculating the area of the site of lesion using the number of pixels. The number of pixels of the calculated area of the site of lesion in each B-scan image is then accumulated and multiplied by the actual area of one pixel and the volume of the site of lesion can thereby be obtained.

However, the actual area of one pixel is different among subjects. This is because, if the scanning width (angle of field) is the same despite different eye axial lengths of the subjects, the image region to be acquired varies. For example, in the case of a subject of myopia, the eye axial length is longer than that of a subject's eye having a normal diopter. Accordingly, the ocular fundus image obtained by scanning spans a wide range and the actual area of one pixel is larger than that of the subject having a normal diopter.

Patent Literature 1 discloses a scheme of scanning light on the ocular fundus of a subject's eye and receiving the reflected light to obtain the ocular fundus image. As described above, in the case of a subject's eye of myopia of which the eye axial length is long, if the scanning angle of field is the same as that for a subject's eye having a normal diopter, the ocular fundus is scanned within a wide range, so that the ocular fundus image to be obtained expands to have a larger area than that of the subject's eye having a normal diopter. Such a configuration is not problematic in an examination in which the change over time of the same subject is qualitatively evaluated, but comparison with others cannot be performed. In Patent Literature 1, therefore, information regarding the eye axial length of the subject's eye is acquired and the scanning angle is adjusted on the basis of the information such that the ocular fundus image becomes substantially the same as that of the subject's eye having a normal diopter. Such control allows the scanning range to be narrow in the case of an eye of myopia of which the eye axial length is long.

PRIOR ART LITERATURE

Patent Literature

[Patent Literature 1] JP2012-11142A

DISCLOSURE OF THE INVENTION

Problems to be Solved by the Invention

Also when a three-dimensional tomographic image is configured from a plurality of tomographic images obtained by scanning the ocular fundus to calculate the volume of a site of lesion, if the eye axial length of the subject's eye is different even though the object to be measured, such as the site of lesion, has the same volume, a different volume is measured to make the quantitative evaluation difficult, which may be problematic.

According to the configuration of Patent Literature 1, the scanning angle is corrected on the basis of the information regarding the eye axial length of subject's eye and the quantitative evaluation of the ocular fundus image is performed thereby to allow the quantitative comparison with others. However, the configuration of correcting the scanning angle as in Patent Literature 1 has a problem in that complex control is required because the scanning mechanism is controlled.

The present invention has been made to solve such problems and an object of the present invention is to provide a volume measuring device, a volume measuring method, and a volume measuring program for a three-dimensional tomographic image that can measure the volume of a certain region of the three-dimensional tomographic image without necessity of complex control.

Means for Solving the Problems

The present invention relates to volume measurement for a three-dimensional tomographic image using a tomographic image capturing unit that captures a tomographic image of an ocular fundus of a subject's eye. The volume measurement is for measuring a volume of a certain region of the three-dimensional tomographic image comprising a plurality of the tomographic images each obtained by scanning the ocular fundus.

The present invention is characterized by comprising:
focusing the tomographic image capturing unit on the ocular fundus in accordance with a diopter of the subject's eye;
outputting an image correction coefficient in accordance with the diopter of the subject's eye, the image correction coefficient being obtained from a relationship between a position of a focus optical system at a time of focusing and a size of an ocular fundus image;
forming the tomographic image by processing a signal output from the tomographic image capturing unit for each scanning;
determining a contour of the certain region in the tomographic image for each tomographic image formed by a tomographic image forming section; and
calculating the volume of the certain region through correcting each area of the certain region defined by the determined contour or its accumulated value using the image correction coefficient in accordance with the diopter of the subject's eye.

Advantageous Effect of the Invention

According to the present invention, the volume of the certain region is corrected using the image correction coefficient in accordance with the diopter of the subject's eye, which is obtained from the relationship between the position of the focus optical system at the time of focusing and the size of the ocular fundus image. Therefore, even for subjects' eyes of different diopters, the influence of the diopter correction is eliminated, the volume of the certain region can be accurately measured, and a quantitative comparison of subjects' eyes of different diopters is possible.

EMBODIMENTS FOR CARRYING OUT THE INVENTION

Figure 1:
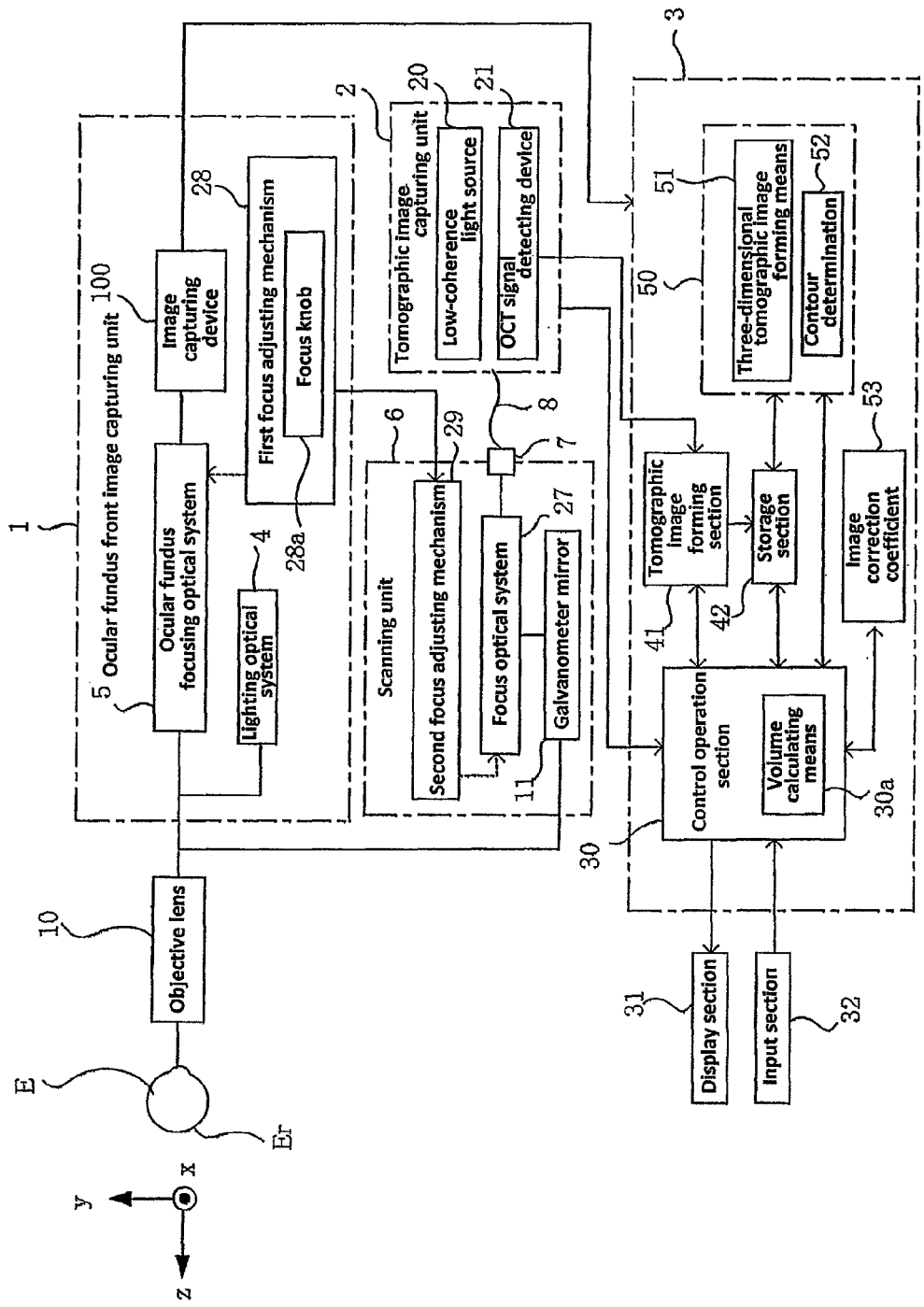
FIG. 1 is a schematic view illustrating the overall configuration for measuring the volume of a three-dimensional tomographic image according to the present invention.

Hereinafter, the present invention will be described in detail on the basis of the examples illustrated in the drawings.

EXAMPLES

FIG. 1 is a block diagram illustrating the whole set of a volume measuring device for measuring the volume of a certain region in a three-dimensional tomographic image of an ocular fundus of a subject's eye. What is denoted by reference numeral 1 is an ocular fundus front image capturing unit (fundus camera) 1 for observation and image capturing of an ocular fundus (retina) Er of a subject's eye E. The ocular fundus front image capturing unit 1 comprises a lighting optical system 4, an ocular fundus focusing optical system 5, an image capturing device 100 that is composed of a two-dimensional CCD and CMOS, and a first focus adjusting mechanism 28.

The lighting optical system 4 comprises an observation light source such as a halogen lamp and an image capturing light source such as a xenon lamp, and the light from these light sources is introduced to the ocular fundus Er via an objective lens 10 to light the ocular fundus Er. The ocular fundus focusing optical system 5 comprises an optical system such as an image capturing lens and a focusing lens and introduces the image capturing light reflected by the ocular fundus Er to the image capturing device 100 along an image capturing optical path to capture images of the ocular fundus Er. The position of the focusing lens is adjusted to match the diopter of the subject's eye by manually operating a focus knob 28a disposed at the first focus adjusting mechanism 28, and its positional information (diopter information) is output using an encoder (not illustrated) disposed inside the focus knob 28a.

Scanning unit 6 comprises a known galvanometer mirror 11 for raster-scanning the light from a low-coherence light source 20 of a tomographic image capturing unit (optical coherence tomography) 2 in the x-direction and y-direction, a focus optical system (diopter correction lens unit) 27, a second focus adjusting mechanism 29, and other necessary components.

The method of scanning the ocular fundus in the present example uses the raster scan, but other methods may also be employed, including a method of scanning the ocular fundus so as to draw circles while successively increasing the radius from the center point and a method of scanning the ocular fundus in a radial fashion from the center point.

The scanning unit 6 is optically connected via a connector 7 and a connecting line 8 to the tomographic image capturing unit 2 which captures tomographic images of the ocular fundus Er.

Figure 2:
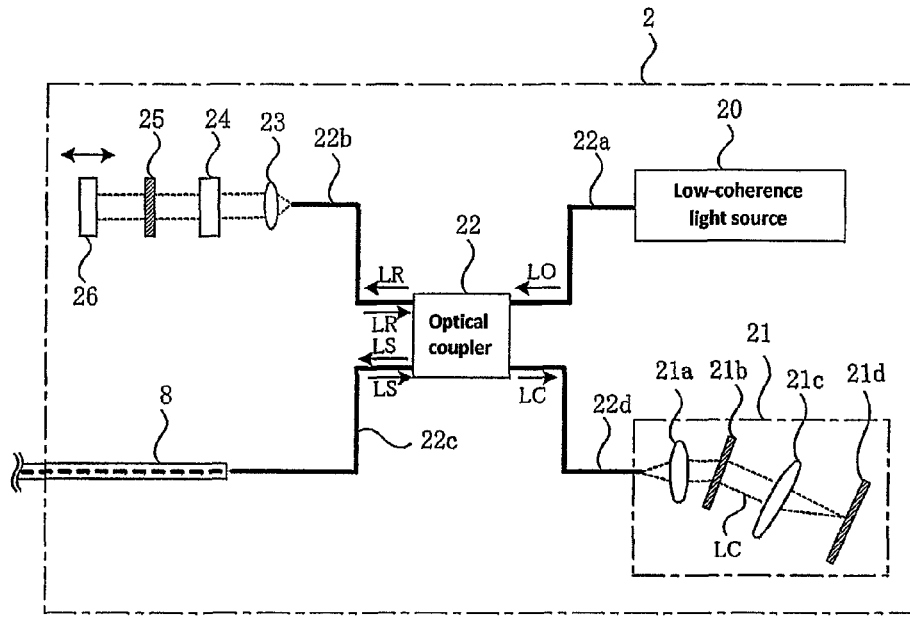
FIG. 2 is an optics view illustrating the detailed configuration of a tomographic image capturing unit.

The tomographic image capturing unit 2 is a known one that operates using the Fourier domain scheme (spectral domain method), for example, and the detailed configuration is illustrated in FIG. 2. The tomographic image capturing unit 2 has a low-coherence light source 20 that emits light of a temporal coherence length of about several micrometers to several tens of micrometers at a wavelength of 700 nm to 1,100 nm.

The low coherence light L0 generated by the low-coherence light source 20 is introduced into an optical coupler 22 through an optical fiber 22a and divided into reference light LR and signal light LS. The reference light LR passes through an optical fiber 22b, a collimator lens 23, a glass block 24, and a density filter 25 and reaches a reference mirror 26 that is movable in the optical axis direction for matching the optical path lengths. The glass block 24 and the density filter 25 function as a delay means for matching the optical path lengths (optical distances) of the reference light LR and signal light LS and also function as a means for matching the dispersion characteristics of the reference light LR and signal light LS.

The signal light LS passes through an optical fiber 22c to be introduced into the scanning unit 6 via an optical fiber inserted in the connecting line 8 and via the connector 7 of FIG. 1 and reaches the ocular fundus Er via the objective lens 10 to scan the ocular fundus in the x-direction and y-direction. The signal light LS reaching the ocular fundus Er is reflected at the ocular fundus Er and tracks back the above path to return to the optical coupler 22.

The reference light LR reflected from the reference mirror 26 and the signal light LS reflected from the ocular fundus Er are superimposed by the optical coupler 22 to be interfering light LC. The interfering light LC is introduced into an OCT signal detecting device 21 via an optical fiber 22d. In the OCT signal detecting device 21, the interfering light LC is caused to be a parallel light flux by a collimator lens 21a, and the parallel light flux is then incident to a diffraction grating 21b to be diffracted and forms an image on a CCD 21d by an imaging lens 21c. The OCT signal detecting device 21 generates an OCT signal that represents information regarding the depth direction (z-direction) of the ocular fundus by the diffracted interfering light.

The focus optical system (diopter correction lens unit) 27 provided in the scanning unit 6 comprises focus lenses 27a and 27b (FIG. 3), among which the focus lens 27b is movable in the optical axis direction and focuses the optical system of the tomographic image capturing unit 2 on the ocular fundus in accordance with the diopter of the subject's eye. The second focus adjusting mechanism 29, which operates together with the first focus adjusting mechanism 28, has a mechanism that obtains diopter information of the focusing lens of the ocular fundus focusing optical system 5 when the examiner rotates the focus knob 28*a* provided in the first focus adjusting mechanism 28 to focus on the ocular fundus. This mechanism thereby controls a stepping motor (not illustrated) to move the focus lens 27*b* so as to automatically focus on the ocular fundus.

Figure 3:
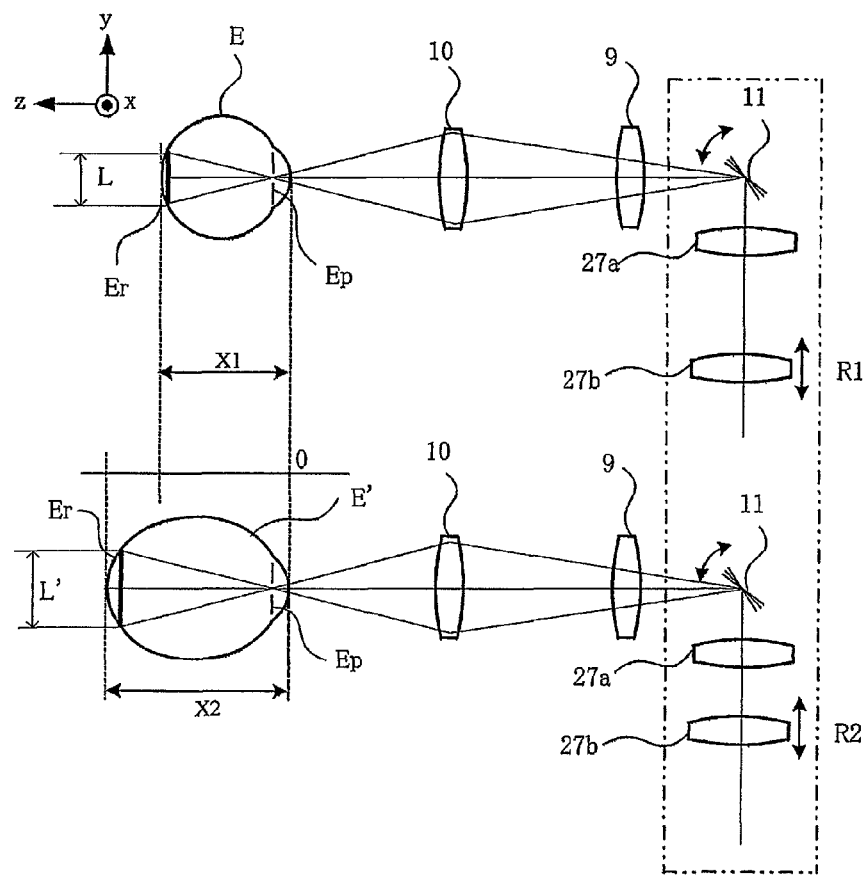
FIG. 3 is a view for explaining a state in which the size of an ocular fundus image varies in accordance with the diopter of the subject's eye.

FIG. 3 illustrates a specific configuration of the focus optical system 27 together with other optical systems. In the figure, the signal light LS having passed through the lenses 27*b* and 27*a* of the focus optical system 27 is scanned in the y-axis direction by the galvanometer 11 of the scanning unit 6 and passes through the objective lens 10 to be incident from the pupil Ep of the subject's eye E to the ocular fundus Er.

What is illustrated in the upper part of FIG. 3 is an example of a subject's eye E having a normal diopter and the eye axial length of the subject's eye is represented by X1. What is illustrated in the lower part is an example of a subject's eye E' of myopia and the eye axial length of the subject's eye E' is represented by X2 which is longer than X1. When the subject's eye E is in focus, the focusing point for the subject's eye E' of myopia is out of alignment. Accordingly, the examiner operates the focus knob 28*a* to adjust the ocular fundus focusing optical system 5 so that the subject's eye E' of myopia is in focus. Through this operation, the diopter information of the ocular fundus focusing optical system 5 is transmitted to the second focus adjusting mechanism and the stepping motor (not illustrated) is driven to allow the focus lens 27*b* to move along the optical path. Thus, the ocular fundus Er of the subject's eye E' can be in focus as illustrated in the lower part of FIG. 3.

The three-dimensional tomographic image measuring device is provided with an image processing device 3 that is composed, for example, of a microcomputer built in the ocular fundus front image capturing unit 1 or a personal computer connected to the ocular fundus front image capturing unit 1 and other necessary components. The image processing device 3 is provided with a control operation section 30 that is composed of a CPU, a RAM, a ROM, and other necessary components. The control operation section 30 executes an image processing program and volume measuring program to control the image processing and volume measuring process as a whole. When the image processing device 3 is provided outside the ocular fundus front image capturing unit 1, the control operation section 30 is connected to the ocular fundus front image capturing unit 1, outputs necessary commands for capturing images of the ocular fundus and its tomographic images, receives necessary information for capturing the images from the ocular fundus front image capturing unit 1, and controls a step of capturing images of the ocular fundus and its tomographic images, a step of image processing, and a step of measuring the volume.

Display section 31 is composed, for example, of a display device such as an LCD and displays images generated or processed by the image processing device 3 and associated information such as information regarding the subject.

Input section 32 has a mouse, keyboard, operation panel, and necessary components, for example, and is used for an operator to give instructions to the image processing device 3 and the like.

The image processing device 3 is provided with a tomographic image forming section 41. The tomographic image forming section 41 is realized as a dedicated electronic circuit that executes a known analyzing method such as the Fourier domain method (spectral domain method) or using an image processing program that is executed by the previously-described CPU, and forms tomographic images of the ocular fundus Er on the basis of the OCT signal detected by the OCT signal detecting device 21. The tomographic images formed by the tomographic image forming section 41 are stored in a storage section 42 that is composed, for example, of a semiconductor memory, hard disk or the like. The storage section 42 further stores the above-described image processing program and volume measuring program and other necessary programs and data.

Image processing section 50 has a three-dimensional tomographic image forming means 51 and a contour determining means 52. The three-dimensional tomographic image forming means 51 forms a three-dimensional tomographic image from a plurality of two-dimensional tomographic images (B-scan images) that are obtained by scanning the ocular fundus Er. The contour determining means 52 determines the contour of a certain region, such as a site of lesion in the tomographic image, for each tomographic image that constitutes the three-dimensional tomographic image. The contour can be determined, for example, by a user specifying the contour, such as using the mouse of the input section 32, and can also be determined using software that automatically extracts the contour.

Image correction coefficient outputting means 53 is composed of a table or two-dimensional map that stores the relationship between a position of the focus optical system at the time of focusing and a size of the ocular fundus image, and outputs an image correction coefficient corresponding to the position on the optical axis of the focus lens 27*b*. This correction coefficient is obtained in a manner as below.

Figure 7:
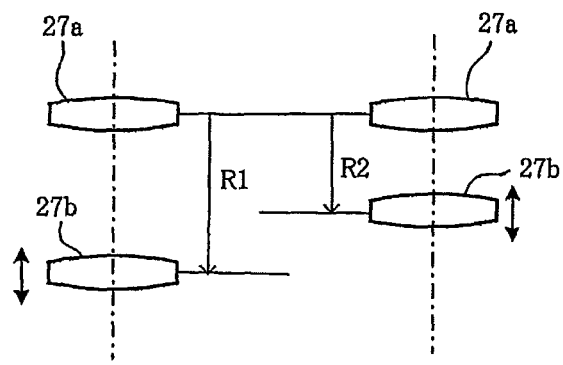
FIG. 7 is a view for explaining an amount of moving a focus lens of a scanning unit for focusing an optical system of the tomographic image capturing unit on the ocular fundus.

When the focus knob 28*a* of the first focus adjusting mechanism 28 is rotated for focusing in accordance with the diopter of the subject's eye, the diopter information is transmitted to the second focus adjusting mechanism 29 and the stepping motor (not illustrated) is driven to vary the position on the optical axis of the focus lens 27*b* of the focus optical system 27, as illustrated in FIG. 3 and FIG. 7. This operation varies the measured length L at the ocular fundus in the y-axis direction and the area of the ocular fundus image which are defined by the scanning range of the galvanometer mirror 11. Accordingly, provided that the measured length of a subject's eye E of a normal diopter is L and the measured length of a subject's eye E' of a diopter different from the normal diopter is L', a ratio L/L' is obtained as a correction coefficient γ when calculating the volume of a measurement region of the three-dimensional tomographic image, while a position (rotation angle=diopter information) R of the focus knob 28*a* at the time of focusing is obtained as the position of the focus optical system 27 at the time of focusing, and the relationship between the focus knob position R and the correction coefficient γ is created in the form of a table.

This table can be created through an experiment or simulation. When the table is obtained by an experiment, values of the diopter and eye axial length of a number of subject's eyes are measured and an approximation formula of the distribution is obtained. The measured length at the time of focusing is calculated using the eye axial length and the tangent of a deflection angle of the galvanometer mirror, and therefore a formula representing the relationship between the focus knob position and the measured length can be obtained. Thus, the relationship between the focus knob position R at the time of focusing and the ratio in association with the measured length L of the normal diopter at that time, i.e. the correction coefficient γ, is obtained as a table.

When the table is obtained by simulation, the eye axial length is calculated at each diopter on a model of eye, and thereafter in a similar procedure to the above, the relationship between the focus knob position R and the correction coefficient γ is obtained as a table.

Figure 8:
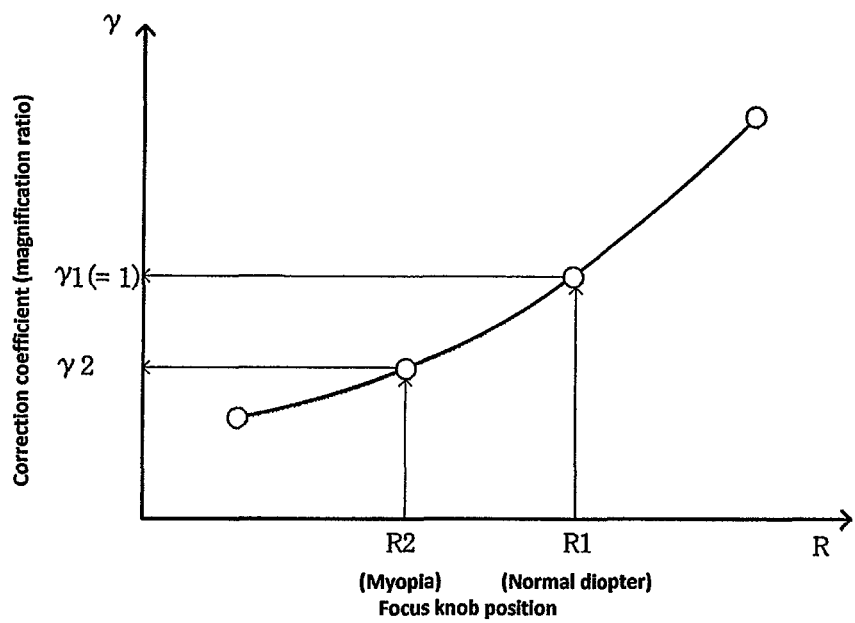
FIG. 8 is a graph illustrating the relationship between a focus knob position and an image correction coefficient.

The table obtained in such a manner is stored as the form of a two-dimensional map as illustrated in FIG. 8 and used as the image correction coefficient outputting means 53.

Volume calculating means 30*a* calculates the volume of a certain region by correcting each area of the certain region, which is defined by the contour determined by the contour determining means 52, using the correction coefficient in accordance with the diopter of the subject's eye and accumulating the area.

Figure 4:
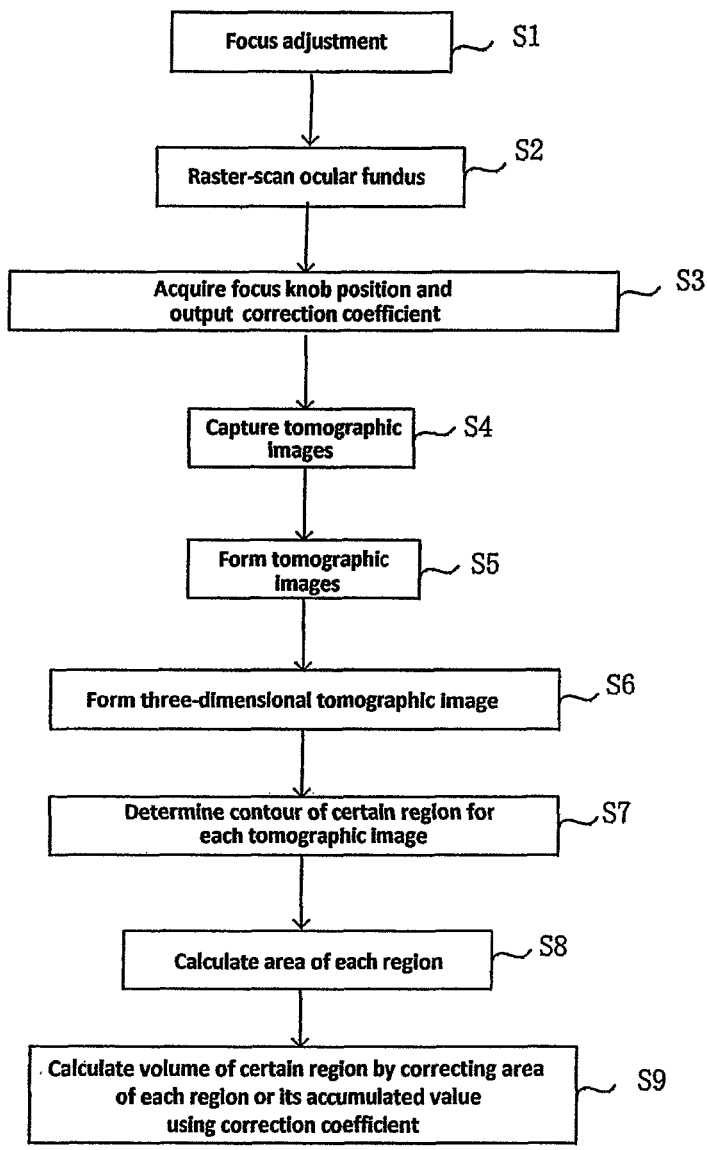
FIG. 4 is a flowchart illustrating the flow of measuring the volume of the three-dimensional tomographic image.

Next, the flow of measuring the volume of the certain region in the three-dimensional tomographic image will be described with reference to the flowchart illustrated in FIG. 4. This measuring process is performed by the control operation section 30 reading out the volume measuring program stored in the storage section 42 to execute it.

Figure 5:
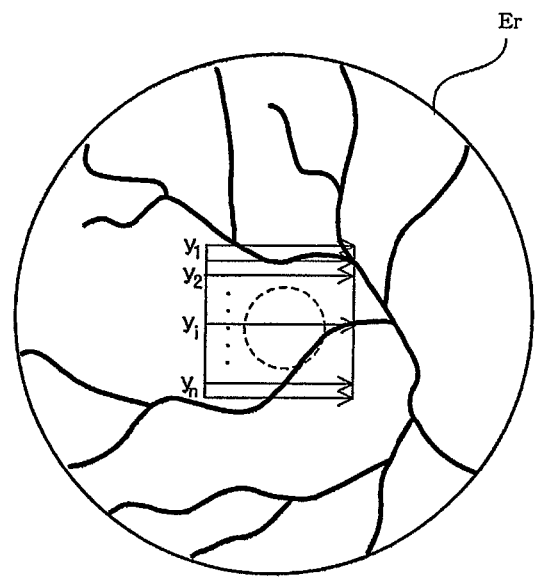
FIG. 5 is a view for explaining a state of raster-scanning an ocular fundus.

After completion of alignment and focus adjustment of the ocular fundus front image capturing unit 1 (step S1), the low-coherence light source 20 of the tomographic image capturing unit 2 is turned on and the scanning unit 6 sweeps the signal light from the tomographic image capturing unit 2 in the x-direction and y-direction to raster-scan the ocular fundus Er (step S2). This state is illustrated in FIG. 5. The region represented by the dashed line in which a macular region of the retina exists is raster-scanned in a direction parallel to the x-axis with n main scanning lines y1, y2, . . . yn.

The signal light LS reflected from the ocular fundus Er is superimposed in the tomographic image capturing unit 2 with the reference light LR reflected from the reference mirror 26. This superimposition generates the interfering light LC and the OCT signal detecting device 21 generates the OCT signal.

After the optical system of the scanning unit 6 focuses accurately on the ocular fundus, the image correction coefficient outputting means 53 is caused to output the correction coefficient γ corresponding to the focus knob position R (step S3). In the case of the subject's eye E having a normal diopter of which the eye axial length is X1, the focus knob position is R1 as illustrated in FIG. 3 and FIG. 7, and the image correction coefficient outputting means 53 outputs the correction coefficient of γ1=1, as illustrated in FIG. 8. In contrast, in the case of the subject's eye E' of myopia of which the eye axial length is X2 longer than X1, the focus knob position at the time of focusing is R2, and the image correction coefficient outputting means 53 outputs the correction coefficient γ2 smaller than 1.

In this manner, the focus adjustment is performed in accordance with the diopter of the subject's eye, and when the optical system of the scanning unit 6 focuses accurately on the ocular fundus, each tomographic image is captured (step S4), the tomographic image forming section 41 forms the tomographic image of the ocular fundus Er on the basis of the OCT signal (step S5), and the tomographic image thus formed is stored in the storage section 42.

Figure 6A:
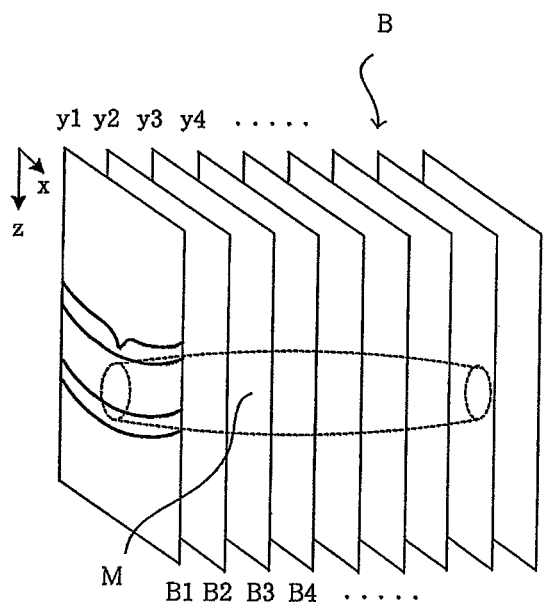
FIG. 6a is a view for explaining a region at which the volume of the three-dimensional tomographic image is measured.

As illustrated in FIG. 6*a*, the three-dimensional tomographic image forming means 51 forms a three-dimensional tomographic image B of the ocular fundus from the xz tomographic images (B-scan images) B1, B2, B3, B4, . . . of the ocular fundus ER which are obtained by raster scan with each main scanning line yi (i=1 to n) (step S6).

Figure 6B:
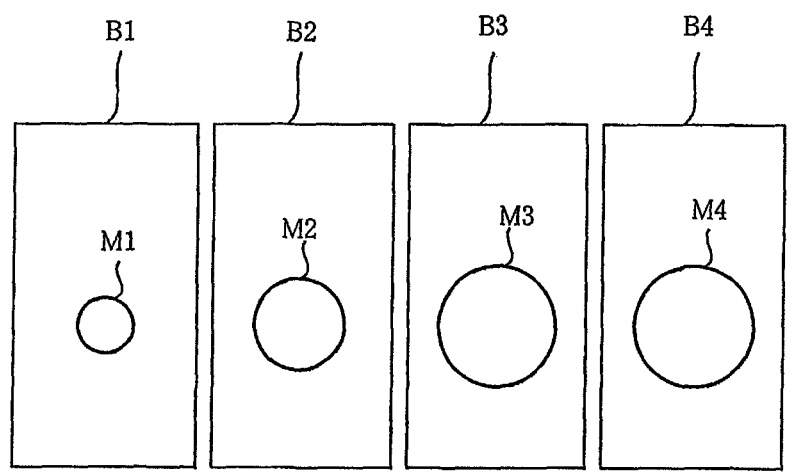
FIG. 6b is a set of views for explaining a certain region extracted in each tomographic image.

The contour determining means 52 determines the contour of a certain region M, such as a site of lesion in the tomographic image, for each tomographic image B1, B2, B3, B4, . . . . The certain region Mi (i=1 to n) of the tomographic image Bi (i=1 to n) is determined by a user specifying the contour of each region Mi, such as using a mouse or input pen of the input section 32 (step S7). The contour of each region Mi may otherwise be determined using software that automatically extracts the contour. FIG. 6*b* illustrates the certain regions M1, M2, M3, and M4 of the tomographic images B1, B2, B3, and B4, which are determined or extracted in such a manner.

After the contour of each region is obtained in this manner, the volume calculating means 30*a* provided with the control operation section 30 calculates the area of each region surrounded by the contour line through summing up the number of pixels (step S8), then multiplies the area of each region by the correction coefficient obtained from the image correction coefficient outputting means 53, and accumulates the product to calculate the volume of the certain region M (step S9). This calculation of the volume may also be performed such that the area of each region is first accumulated and the accumulated area is multiplied by the correction coefficient to obtain the volume, rather than multiplying the area of each region by the correction coefficient for correction and accumulating the corrected area of each region.

In the case of the subject's eye E having a normal diopter, for example, the result is the same as that without correction because of the correction coefficient of γ=1, but in the case of the subject's eye E' of myopia, the area of each region takes a smaller value because the correction coefficient is smaller than 1. Accordingly, the volume of the region M, which is the accumulated value of the area of each region, also takes a smaller value, and it is thus possible to correct the value of volume which varies due to diopter correction.

According to the present invention, the volume of a measurement region such as a site of lesion is corrected using a correction coefficient for correcting images that are scaled by focus adjustment in accordance with the diopter of the subject's eye to images that are not scaled. Therefore, even for subjects' eyes of different diopters, the influence of the diopter correction is eliminated and a quantitative comparison of subjects' eyes of different diopters is possible.

DESCRIPTION OF REFERENCE NUMERALS

1 Ocular fundus front image capturing unit
2 Tomographic image capturing unit
3 Image processing device
4 Lighting optical system
5 Ocular fundus focusing optical system
6 Scanning unit
20 Low-coherence light source
21 OCT signal detecting device
28 First focus adjusting mechanism
28*a* Focus knob
29 Second focus adjusting mechanism
30 Control operation section
30*a* Volume calculating means
31 Display section
32 Input section
41 Tomographic image forming section
42 Storage section 51 Three-dimensional tomographic image forming means
52 Contour determining means
53 Image correction coefficient outputting means

The invention claimed is:

1. A volume measuring device for a three-dimensional tomographic image, the volume measuring device comprising a tomographic image capturing unit that captures a tomographic image of an ocular fundus of a subject's eye, the volume measuring device being for measuring a volume of a certain region of the three-dimensional tomographic image comprising a plurality of the tomographic images each obtained by scanning the ocular fundus, the volume measuring device further comprising:
a focus optical system that focuses the tomographic image capturing unit on the ocular fundus in accordance with a diopter of the subject's eye;
an output means that outputs an image correction coefficient in accordance with the diopter of the subject's eye, the image correction coefficient being obtained from a relationship between a position of the focus optical system at a time of focusing and a size of an ocular fundus image;
a tomographic image forming section that forms the tomographic image by processing a signal output from the tomographic image capturing unit for each scanning;
a contour determining means that determines a contour of the certain region in the tomographic image for each tomographic image formed by the tomographic image forming section; and
a calculating means that calculates the volume of the certain region through correcting each area of the certain region defined by the determined contour or its accumulated value using the image correction coefficient in accordance with the diopter of the subject's eye.

2. The volume measuring device for a three-dimensional tomographic image as recited in claim 1, wherein the image correction coefficient is obtained from focus position information at the time of focusing and a magnification ratio of the ocular fundus image on a basis of a relationship between the diopter of the subject's eye and an eye axial length, wherein the relationship is obtained by an experiment or simulation.

3. The volume measuring device for a three-dimensional tomographic image as recited in claim 1, wherein the contour of the certain region is determined by a user specifying the contour.

4. The volume measuring device for a three-dimensional tomographic image as recited in claim 1, wherein the contour of the certain region is determined using software that automatically extracts the contour.

5. A volume measuring method for a three-dimensional tomographic image, the volume measuring method using a tomographic image capturing unit that captures a tomographic image of an ocular fundus of a subject's eye, the volume measuring method being for measuring a volume of a certain region of the three-dimensional tomographic image comprising a plurality of the tomographic images each obtained by scanning the ocular fundus, the volume measuring method comprising:
a step of focusing the tomographic image capturing unit on the ocular fundus in accordance with a diopter of the subject's eye;
a step of outputting an image correction coefficient in accordance with the diopter of the subject's eye, the image correction coefficient being obtained from a relationship between a position of a focus optical system at a time of focusing and a size of an ocular fundus image;
a step of forming the tomographic image by processing a signal output from the tomographic image capturing unit for each scanning;
a step of determining a contour of the certain region in the tomographic image for each tomographic image formed by a tomographic image forming section; and
a step of calculating the volume of the certain region through correcting each area of the certain region defined by the determined contour or its accumulated value using the image correction coefficient in accordance with the diopter of the subject's eye.

6. A volume measuring program for a three-dimensional tomographic image, the volume measuring program causing a computer to execute the volume measuring method as recited in claim 5.

* * * * *